US009063056B2

(12) United States Patent
Fasbender

(10) Patent No.: US 9,063,056 B2
(45) Date of Patent: Jun. 23, 2015

(54) IMAGING DETECTOR AND METHOD FOR OPERATING AN IMAGE DETECTOR

(71) Applicant: Siemens Aktiengesellschaft, Munich (DE)

(72) Inventor: Robert Fasbender, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/053,656

(22) Filed: Oct. 15, 2013

(65) Prior Publication Data
US 2014/0110586 A1    Apr. 24, 2014

(30) Foreign Application Priority Data

Oct. 18, 2012  (DE) .......................... 10 2012 219 041

(51) Int. Cl.
| | | |
|---|---|---|
| G01T 1/10 | (2006.01) | |
| G01N 23/04 | (2006.01) | |
| G01T 1/24 | (2006.01) | |
| A61B 6/00 | (2006.01) | |

(52) U.S. Cl.
CPC ............ *G01N 23/04* (2013.01); *G01T 1/24* (2013.01); *A61B 6/42* (2013.01); *A61B 6/4233* (2013.01); *A61B 6/4291* (2013.01)

(58) Field of Classification Search
CPC .............................. G06K 9/209; H04N 9/045
USPC ............ 250/361 R, 370.01–370.15; 378/98.8
See application file for complete search history.

(56) References Cited

U.S. PATENT DOCUMENTS

| | | |
|---|---|---|
| 6,683,934 B1 | 1/2004 | Hibbsopsahl-Ong |
| 6,816,572 B2 | 11/2004 | Avinash |
| 7,180,366 B2 | 2/2007 | Colbeth |
| 8,111,803 B2 | 2/2012 | Basu |
| 2003/0103151 A1 | 6/2003 | Luo |
| 2003/0169848 A1 | 9/2003 | Avinash |
| 2003/0169850 A1 | 9/2003 | Kump |
| 2005/0226375 A1 | 10/2005 | Claus |
| 2006/0119427 A1 | 6/2006 | Colbeth |
| 2007/0081628 A1 | 4/2007 | Dasani et al. |
| 2011/0133094 A1 | 6/2011 | Partain |

FOREIGN PATENT DOCUMENTS

| | | | |
|---|---|---|---|
| DE | 102007058447 A1 | 6/2009 | |
| JP | 2001267543 A * | 9/2001 | .............. H01L 27/14 |
| WO | WO 2006044692 A2 | 4/2006 | |

OTHER PUBLICATIONS

J.A.Rowlands; The physics of computed radiography; in: Physics in Medicine and Biology, vol. 47, 2002, S. R123-R166, XP002293656; IOP Publishing Ltd.; 47; 2002; GB; Nov. 20, 2002.
E. Matsinos: "Current status of the CBCT project at Varian Medical Systems" Medical Imaging 2005: Physics of Medical Imaging, Proceedings of SPIE vol. 5745, p. 340-351; 2005.

(Continued)

*Primary Examiner* — Kiho Kim
(74) *Attorney, Agent, or Firm* — Harness, Dickey & Pierce, P.L.C.

(57) ABSTRACT

An image detector is disclosed, in particular for X-ray radiation. In an embodiment, the image detector includes a regular arrangement of image pixels including a plurality of detector pixels, wherein at least two of the detector pixels of an image pixel differ with regard to their sensitivity.

18 Claims, 1 Drawing Sheet

(56) References Cited

OTHER PUBLICATIONS

The dual-dose imaging technique: a way to enhance the dynamic range of X-ray detectors; E. Matsinos et al.: "The dual-dose imaging technique: a way to enhance the dynamic range of X-ray detectors", Jul. 4, 2006, http://arxiv.org/abs/physics/0607024; 2006.

Status and Prospects of Digital Detector Technology for CR and DR; U. Neitzel: "Status and Prospects of Digital Detector Technology for CR and DR", Radiation Protection Dosimetry (2005), vol. 114, Nos. 1-3, pp. 32-38; 2005.

Optimal phosphor thickness for portal imaging; Jean-Pierre Bissonnette: "Optimal phosphor thickness for portal imaging", Med. Phys. 24 (6), Jun. 1997, Am. Assoc. Phys. Med., p. 803-814; 1997.

E. Matsinos et al., "The dual-gain mode: a way to enhance the dynamic range of X-ray detectors", Preprint physics/0607021, physics.med-ph, pp. 1-21; Jul. 4, 2006.

* cited by examiner

IMAGING DETECTOR AND METHOD FOR OPERATING AN IMAGE DETECTOR

PRIORITY STATEMENT

The present application hereby claims priority under 35 U.S.C. §119 to German patent application number DE 102012219041.4 filed Oct. 18, 2012, the entire contents of which are hereby incorporated herein by reference.

FIELD

At least one embodiment of the invention generally relates to an image detector, in particular for X-ray radiation, comprising a regular arrangement of image pixels having a plurality of detector pixels, and/or to a method for operating a corresponding image detector.

BACKGROUND

X-ray detectors used, for example, for examining objects or patients by way of an imaging method are intended to have the highest possible dynamic range or contrast range relative to the radiation power or the X-ray dose, since the relevant information is obtained precisely by the detection of local intensity differences in the X-ray radiation impinging on an X-ray detector and is thus detected as contrast differences.

In this case, on the one hand, it is often necessary to detect very large intensity differences, that is to say for example intensity differences between X-ray radiation which propagates past the object to be examined or past the patient to be examined in the direction of the X-ray detector and X-ray radiation which transmits through the object to be examined or the patient to be examined, and, on the other hand, very fine intensity differences are intended to be detected in order, on the basis of these intensity differences, to be able to differentiate between different materials within the volume of the object to be examined or between different types of tissue in the body of the patient to be examined.

However, the dynamic range of present-day X-ray detectors typically does not suffice to image the entire desired dynamic range, that is to say the desired contrast value range with the desired contrast resolution. Modern digital X-ray detectors instead generally have an adjustable sensitivity setting by means of which an operator can adapt the available dynamic range of the detector to the respective situation, such that at least the most important dynamic range for an examination is detected during an examination of an object or patient. If a greater dynamic range is nevertheless intended to be detected, a plurality of recordings of the object or patient with different settings for the exposure are made successively in order in this way to detect a subrange of the dynamic range with each recording.

Since, in most cases, the factor limiting the dynamic range is not to be found in the X-ray-sensitive sensor elements themselves, but rather in the downstream read-out electronic system, there are various approaches for subsequently conditioning the measurement signals of the X-ray-sensitive sensor elements in order in this way to extend the dynamic range or at least expediently predefine the available range of values.

SUMMARY

At least one embodiment of the invention is directed to an improved image detector and a method for operating a corresponding image detector.

The image detector, in at least one embodiment, is preferably designed for metrologically detecting X-ray radiation and comprises a regular arrangement of image pixels having a plurality of detector pixels or subpixels. In this case, at least two of the detector pixels of an image pixel differ with regard to their sensitivity, such that they generate different measurement signals for example upon being identically exposed to X-ray radiation. The differing detector pixels of an image pixel are therefore configured in such a way that they are used to metrologically detect and in this way image different subranges of a provided dynamic range or contrast range of a radiation power or of an X-ray dose. It is thereby possible to image a larger dynamic range with only one recording or one exposure, wherein the detected dynamic range, that is to say the detected contrast range and/or the contrast resolution, rises with an increasing number of different detector pixels per image pixel. In this case, the measurement signals of the detector pixels of an image pixel are preferably used to generate image data which are represented by way of exactly one pixel for example on a monitor.

At least one embodiment of the method serves for operating an image detector, and in particular an image detector of the type described above. In this case, for generating image data, a provided dynamic range of a radiation power, in particular a provided dynamic range of an X-ray dose, for the image data is split into subranges, which can also overlap, and each subrange is metrologically detected by means of a regular arrangement of detector pixels, wherein for imaging the provided dynamic range the measurement signals of the detector pixels of the regular arrangements are combined with one another.

BRIEF DESCRIPTION OF THE DRAWINGS

Example embodiments of the invention are explained in greater detail below with reference to schematic drawings, in which.

Mutually corresponding parts are in each case provided with the same reference signs in all the figures.

DETAILED DESCRIPTION OF THE EXAMPLE EMBODIMENTS

Figure 1:
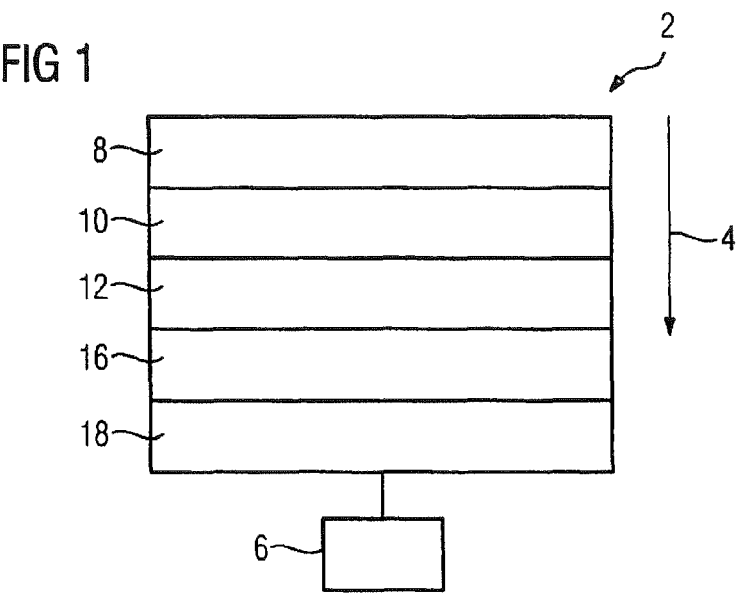
FIG. 1 shows an X-ray detector in a sectional illustration.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The image detector, in at least one embodiment, is preferably designed for metrologically detecting X-ray radiation and comprises a regular arrangement of image pixels having a plurality of detector pixels or subpixels. In this case, at least two of the detector pixels of an image pixel differ with regard to their sensitivity, such that they generate different measurement signals for example upon being identically exposed to X-ray radiation. The differing detector pixels of an image pixel are therefore configured in such a way that they are used to metrologically detect and in this way image different subranges of a provided dynamic range or contrast range of a radiation power or of an X-ray dose. It is thereby possible to image a larger dynamic range with only one recording or one exposure, wherein the detected dynamic range, that is to say the detected contrast range and/or the contrast resolution, rises with an increasing number of different detector pixels per image pixel. In this case, the measurement signals of the detector pixels of an image pixel are preferably used to generate image data which are represented by way of exactly one pixel for example on a monitor.

Dynamic range is generally understood to mean the ratio between the maximum and the minimum of the radiation power/intensity. As a result of the arrangement of detector pixels of differing sensitivity with regard to the dynamic range, therefore, one type of the detector pixels is designed in particular for a small dynamic range, and the other type of the detector pixels is designed for a large dynamic range.

An X-ray detector configured in this way is preferably used in the field of image guided radiotherapy (IGRT) since here, on the one hand, a very large dynamic range is particularly advantageous and since, on the other hand, the resolution required here, in the sense of pixels per represented image, for the X-ray images generated by way of the imaging method is comparatively low. The number of required image pixels per area is accordingly typically lower, for example in comparison with the requirements in the case of computer aided tomography scanners for diagnostics, and production of image pixels having a plurality of detector pixels or subpixels is technically easier to realize.

Furthermore, a configuration of the image detector is preferred in which the detector pixels are designed as so-called indirect X-ray radiation sensors and therefore each comprise a light-sensitive semiconductor sensor and a scintillator volume. In this case, the scintillator volumes are furthermore preferably designed for the highest possible quantum efficiency, such that as far as possible all X-ray quanta which impinge on a scintillator volume generate therein light from the frequency range of so-called visible light.

In accordance with one configuration variant, the differing sensitivity of the detector pixels is realized by the light-sensitive semiconductor sensors being configured differently. That is to say that, by way of corresponding adaptations in the process control during the production of the semiconductor sensors, different semiconductor sensors are produced for the detector pixels which differ with regard to their sensitivity, wherein the differing semiconductor sensors react differently to incident light. Therefore, if light with the same frequency and the same intensity impinges for example on two different semiconductor sensors, then different electrical signals are nevertheless generated by means of the corresponding semiconductor sensors. This can be achieved for example by doping semiconductor material for the semiconductor sensors to different extents.

As an alternative or in addition thereto, at least one detector pixel of each image pixel having a plurality of detector pixels, for manipulating the sensitivity, has a filter element, wherein such a filter element, for example according to the principle of two polarization filters disposed one behind the other, filters out a predetermined portion of the light emitted from the upstream scintillator volume before said light reaches the assigned light-sensitive semiconductor sensor. Alternatively, filter elements are provided which act as frequency-band-splitting color filters and accordingly predominantly filter out light from a specific frequency range.

In an advantageous development, for manipulating the sensitivity a plurality of detector pixels of each image pixel having a plurality of detector pixels have a filter element, wherein at least two filter elements of each image pixel having a plurality of detector pixels differ. In this case, therefore, a corresponding image pixel comprises a plurality of detector pixels and the detector pixels have different filter elements that differ in particular with regard to the light absorptivity.

Furthermore, the filter elements are preferably designed in such a way that they transmit a predefined intensity portion of the impinging electromagnetic radiation, that is to say in particular the impinging X-ray radiation, for a metrological detection. In this case, it should be taken into consideration that corresponding image detectors are typically used together with a radiation source whose properties are known or can be predefined by a corresponding driving system. Accordingly, the dynamic range, on the one hand, and the contrast value range of the electromagnetic radiation impinging on the image detector during operation, on the other hand, are known and, by way of a suitable configuration of the filter elements, it is accordingly possible to predefine what portion is absorbed by the filter elements and what portion transmits through the filter elements. If the image detector then has for example two detector pixels per image pixel, wherein one detector pixel per image pixel comprises a filter element, the filter elements are preferably designed in such a way that they absorb 50% of the radiation intensity of the impinging electromagnetic radiation. In this case, the dynamic range or contrast range is then subdivided into two subranges of identical magnitude.

For the case where the electromagnetic radiation impinging on the image detector is not monochromatic, the filter elements are preferably designed in such a way that they have a substantially constant absorptivity in the entire expected frequency range of the impinging electromagnetic radiation. That is to say that the filter elements are preferably precisely not used for frequency-selective filtering, but rather for weakening the impinging radiation power or radiation intensity, such that the detector pixels with a filter element metrologically detect a reduced radiation intensity or radiation power.

Particularly in the case of using the image detector for detecting X-ray radiation with the aid of a scintillator, the filter elements are preferably positioned on that side of the scintillator which faces away from the X-ray radiation source, and the filter elements are accordingly designed for manipulating electromagnetic radiation in the frequency range of so-called visible light.

In favor of the lowest possible production outlay for corresponding image detectors, the image detectors preferably have a structured color filter, designed in particular as a layer, in such a way that subregions of the color filter form the filter elements. Therefore, if for example two detector pixels are provided per image pixel, which are strung together in two orthogonal directions, then the color filter has a checkered structuring, at least in the case of square configuration of the detector pixels, wherein for example one half of these checkered structure elements are transparent to the light emitted by the scintillator, while the other elements filter out at least part of this light, more precisely of the light power or the light intensity.

A configuration of the image detector is furthermore advantageous in which the image detector has only image pixels designed in the same way, since the technical outlay for production is particularly low as a result. Alternatively, the image detector is constructed from differently configured image pixels, wherein, by way of example, image pixels having a plurality of detector pixels are arranged in a central region of the image detector, while image pixels having only one detector pixel are positioned in a surrounding edge region of the image detector. In accordance with another configuration, provision is made for the different image pixels to differ by virtue of the fact that the detector pixels of different image pixels differ with regard to their sensitivity.

The number of detector pixels per image pixel is expediently adapted to the respective purpose of use for which the corresponding image detector is provided. However, preference is given, in particular, to a configuration in which each image pixel is constructed from four detector pixels of the same size, wherein with further preference all the image pixels of the image detector are configured in the same way.

Furthermore, the image detector advantageously comprises a read-out electronic system configured in such a way that each detector pixel comprises a read-out unit, wherein all the read-out units are constructed in the same way. With further preference, the electric signals generated with the aid of the read-out units are then amplified in the same way, such that the differing sensitivity of detector pixels is realized precisely not by a specific configuration of the read-out electronic system and in particular not by an individually adapted signal amplification, but rather preferably solely by a targeted coupling-out or absorption of electromagnetic radiation during the process of measurement signal generation by way of the detector pixels.

The extension of the dynamic range is therefore achieved first of all solely by virtue of the measurement signals read out by way of the read-out units being manipulated by a reconfiguration of the detector pixels, and not by virtue of the measurement signals read out being suitably conditioned. An expedient conditioning of the measurement signals is preferably additionally performed, however, wherein a wide variety of conditioning possibilities are implemented here depending on the purpose of use. In this regard, provision is made, for example, for feeding the signals of each detector pixel in parallel into different amplifier stages having different signal amplification characteristics, in order to provide a particularly expedient amplifier stage in each case for different ranges of values of the signals. Alternatively, the signals, for example for further processing, can firstly be electronically compressed by being fed to an analog computing circuit.

Preferably, however, the measurement signals read out by way of the read-out units are all amplified in the same way, subsequently digitized and then fed to an evaluation unit. The corresponding evaluation unit then provides an operator with different conditioning algorithms for selection, from which the operator, depending on the situation, selects a suitable algorithm for the respective data set of measurement signals. The different algorithms are then adapted for example to the different operating modes of a medical device in which the corresponding image detector is used. Moreover, the conditioning of the measurement signals fed to the evaluation unit does not necessarily take place in the context of image data generation; instead, subsequent conditioning of the measurement signals is also possible at any time.

If, by way of example, the image detector has n×m image pixels and each image pixel comprises i detector pixels or subpixels having different sensitivities, then n×m×i signals per recording are available in the evaluation unit and are then combined with one another by suitable algorithms. In this case, for example, firstly i individual images are created, which are in each case constructed from n×m pixels representing the signals of the detector pixels having the same sensitivity i. These individual images can then be represented on a monitor, for example. For comparability between the individual images, it is additionally possible to predefine a correction factor for each individual image, with the aid of which the signal values on which the individual image is based are multiplied, for example.

Besides a separate representation of the individual images, provision is furthermore made for superimposing the individual images or combining their information with one another. The final image then constitutes for example a type of collage composed of the individual images, wherein the individual regions of the final image reproduce the corresponding regions of one or more individual images. Therefore, if for example two individual images are available, then the final image shows for example the central region of the first individual image in the central region and the edge region of the other individual image in the surrounding edge region.

Threshold values or signal value ranges are preferably taken into account in the selection of measurement signals of detector pixels which are taken into account when creating the final image. For measurement signals of detector pixels having different sensitivities, in this case different threshold values or signal ranges are typically predefined, wherein the individual signal ranges preferably overlap.

Besides a collage-like combination of the individual images, provision is likewise made for making available for selection a conditioning in which as it were the pixels of the individual images are combined with one another in a weighted manner. That is to say that the measurement signals of the detector pixels of an image pixel are firstly weighted, that is to say multiplied by a factor, for example, and are subsequently combined with one another, that is to say added, for example, so as then to represent a pixel on the basis of the summation signal.

At least one embodiment of the method serves for operating an image detector, and in particular an image detector of the type described above. In this case, for generating image data, a provided dynamic range of a radiation power, in particular a provided dynamic range of an X-ray dose, for the image data is split into subranges, which can also overlap, and each subrange is metrologically detected by means of a regular arrangement of detector pixels, wherein for imaging the provided dynamic range the measurement signals of the detector pixels of the regular arrangements are combined with one another.

Furthermore, image data generation is preferably performed in such a way that in regions of the X-ray detector in which electromagnetic radiation having a radiation power above a threshold value impinges, the measurement signals from detector pixels with a filter element are taken into account to generate pixels for an image, while in the regions in which electromagnetic radiation having a radiation power below said threshold value impinges, the measurement signals from detector pixels without a filter element are used for generating pixels.

The image detector described below is designed as an X-ray detector 2 for metrologically detecting X-ray radiation which is generated by means of an X-ray tube (not concomitantly illustrated) and which is used for examining a patient positioned between the X-ray tube and the X-ray detector 2 by way of an imaging method according to a manner known per se.

In this case, the X-ray detector 2 has a layered construction depicted schematically in FIG. 1 and comprising five layers adjoining one another in a layer sequence direction 4, and also an evaluation unit 6.

As the topmost layer, the X-ray detector 2 has an anti scatter grid 8, which serves for absorbing scattered X-ray radiation. The subsequent second layer is formed by a scintillator 10, for example composed of $Gd_2O_2S$:Tb, in which the non-scattered X-ray radiation passing through the anti scatter grid 8 generates light in the range of the so-called visible spectrum, for example 550 nm. Depending on the purpose of use, instead of the anti scatter grid 8, alternatively a metal plate, in particular a Cu plate, as topmost layer is disposed upstream of the scintillator 10 or else a functional unit disposed upstream is entirely dispensed with.

The light propagating in the layer sequence direction 4 subsequently impinges on a structured color filter 12, which forms the third layer of the X-ray detector 2. Transversely with respect to the layer sequence direction 4, the structured color filter 10 has in a regular arrangement regions which are transparent to the light from the scintillator 10, while the other regions, which are likewise uniformly distributed and arranged like a matrix, as filter elements 14 absorb part of the light which impinges on the filter elements 14.

The light passing through the structured color filter 12 subsequently impinges on the fourth layer, which is constructed from light-sensitive semiconductor sensors 16, and is used there for generating electrical measurement signals, which are read out and amplified with the aid of read-out units 18 in the fifth layer.

For generating image data and ultimately for generating images constructed from pixels, the X-ray detector 2 has, besides a layered construction in the layer sequence direction 4, a matrix-like arrangement of image pixels, that is to say a cellular construction transversely with respect to the layer sequence direction 4, wherein the image pixels are strung together in each case in two orthogonal directions transversely with respect to the layer sequence direction 4. In this case, the image pixels 20 are of square configuration having an edge length of 400 µm and each image pixel 20 is constructed from four square detector pixels 22 having an edge length of 200 µm which are positioned in a 2×2 arrangement relative to one another.

Each detector pixel 22 furthermore comprises a read-out unit 18, a semiconductor sensor 16, a volume element of the color filter 12, a volume element of the scintillator 10 and a volume element of the anti scatter grid 8, wherein these functional units are arranged congruently one above another in the layer sequence direction 4.

Figure 2:
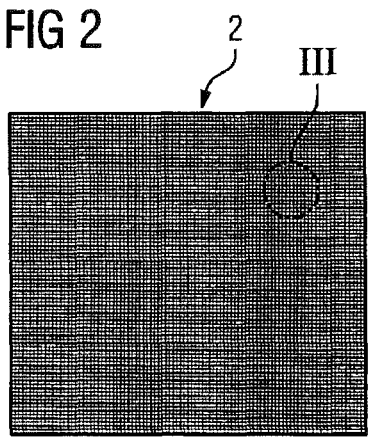
FIG. 2 shows a layer of the X-ray detector in a plan view.
Figure 3:
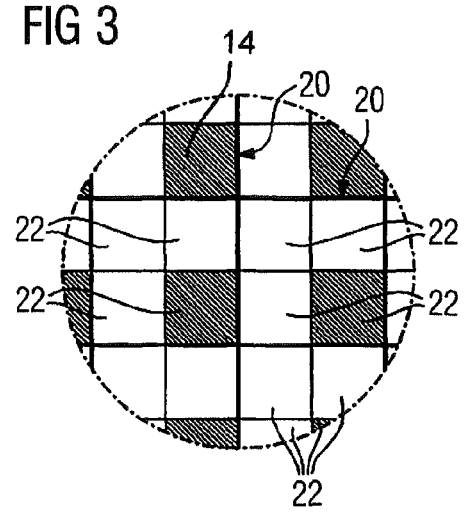
FIG. 3 shows an excerpt from the layer of the X-ray detector in an enlarged illustration.

The matrix-like arrangement of the detector pixels 22 is illustrated schematically in FIG. 2 and a subregion of this arrangement is depicted in an enlarged manner in FIG. 3. The image pixels 20 are marked here by thicker lines, while the detector pixels 22 are identified by thinner lines. The hatched region marks the position of the filter elements 14, that is to say of the regions of the color filter 12 which are not transparent to the impinging light, but rather absorb part of the light.

In the example embodiment, therefore, exactly one detector pixel 22 of each image pixel 20 has an absorbent filter element 14 which covers the corresponding detector pixel 22 over the complete area, while the other detector pixels 22 of the image pixel 20 do not have an absorbent filter element 14.

With the aid of each detector pixel 22, a measurement signal is generated when X-ray radiation impinges, which measurement signal together with the other measurement signals of the other detector pixels 22 is communicated as part of a data packet to the evaluation unit 6, where the data packet is stored in a memory. For image representation, the measurement signals of the data packet are conditioned by means of an algorithm stored in the evaluation unit 6 and are finally displayed as an image data set on a screen.

In the simplest case, the measurement signals of a data set communicated to the evaluation unit 6 are conditioned in such a way that in regions of the X-ray detector 2 in which X-ray radiation having an intensity above a threshold value impinges, the measurement signals of the detector pixels 22 with a filter element are used to generate pixels for an image, while in the regions in which X-ray radiation having an intensity below the threshold value impinges, the signals of the detector pixels 22 which do not comprise an absorbent filter element 14 are used for generating pixels. Since each image pixel 20 is provided with more detector pixels 22 without an absorbent filter element 14 than detector pixels 22 with a corresponding filter element 14, the final image has a higher resolution, in the sense of more pixels per area in the representation, in regions having an intensity below the threshold value than in regions having an intensity above said threshold value.

The invention is not restricted to the example embodiment described above. Rather, other variants of the invention can also be derived therefrom by the person skilled in the art, without departing from the subject matter of the invention. In particular, all individual features described in connection with the example embodiment can furthermore also be combined with one another in another way, without departing from the subject matter of the invention.

What is claimed is:

1. An image detector, comprising:
a regular arrangement of image pixels including a plurality of detector pixels, at least two of the detector pixels of an image pixel differing with regard to sensitivity, such that the at least two of the detector pixels are used to metrologically detect different subranges of a provided dynamic range of a radiation power, wherein each detector pixel comprises a light-sensitive semiconductor sensor, and wherein the detector pixels that differ with regard to their sensitivity have different semiconductor sensors.

2. The image detector of claim 1, wherein, for manipulating the sensitivity, at least one detector pixel, of each image pixel including a plurality of detector pixels, includes a filter element.

3. The image detector of claim 2, wherein the filter elements are designed such that the filter elements transmit a predefined intensity portion of the impinging electromagnetic radiation for a metrological detection.

4. The image detector of claim 3, wherein the filter elements are designed such that the filter elements include a substantially constant absorptivity in the entire expected frequency range of the impinging electromagnetic radiation.

5. The image detector of claim 2, wherein each filter element is disposed downstream of a scintillator.

6. The image detector of claim 2, wherein the image detector includes a structured color filter, such that subregions of the color filter form the filter elements.

7. The image detector of claim 1, wherein, for manipulating the sensitivity, a plurality of detector pixels, of each image pixel including a plurality of detector pixels, include a filter element, and wherein at least two filter elements of each image pixel including a plurality of detector pixels differ.

8. The image detector of claim 7, wherein the filter elements are designed such that the filter elements transmit a predefined intensity portion of the impinging electromagnetic radiation for a metrological detection.

9. The image detector of claim 8, wherein the filter elements are designed such that the filter elements include a substantially constant absorptivity in the entire expected frequency range of the impinging electromagnetic radiation.

10. The image detector of claim 1, wherein the image detector includes only image pixels designed in the same way.

11. The image detector of claim 1, wherein each image pixel is constructed from four detector pixels of the same size.

12. The image detector of claim 1, wherein, for forming a read-out electronic system, each detector pixel includes a read-out unit, and wherein all the read-out units are constructed in the same way.

13. The image detector of claim 1, further comprising a read-out electronic system, designed such that the signals of all the detector pixels are amplified in the same way.

14. A method for operating an image detector, comprising:
splitting into subranges, for generation of image data, a provided dynamic range of a radiation power for the image data, each subrange being metrologically detectable by way of a regular arrangement of detector pixels, wherein each detector pixel comprises a light-sensitive semiconductor sensor, and wherein the detector pixels that differ with regard to their sensitivity have different semiconductor sensors; and
combining with one another, for imaging of the provided dynamic range, the measurement signals of the detector pixels of the regular arrangements.

15. The method of claim 14, wherein, in regions of the image detector in which electromagnetic radiation including a radiation power above a threshold value impinges, the measurement signals from detector pixels with a filter element are used to generate pixels for an image, and in regions in which electromagnetic radiation including a radiation power below the threshold value impinges, the measurement signals from detector pixels without a filter element are used for generating pixels.

16. The image detector of claim 1, wherein the image detector is for X-ray radiation.

17. The image detector of claim 16, wherein the provided dynamic range is a provided dynamic range of an X-ray dose.

18. The method of claim 14, wherein the provided dynamic range of a radiation power for the image data is a provided dynamic range of an X-ray dose.

* * * * *